United States Patent [19]

Kono et al.

[11] Patent Number: 4,820,824

[45] Date of Patent: Apr. 11, 1989

[54] MITOMAYCIN COMPOUNDS

[75] Inventors: Motomichi Kono, Tokyo; Masaji Kasai, Kanagawa; Yutaka Saito, Tokyo; Makoto Morimoto; Tadashi Ashizawa, both of Shizuoka, all of Japan

[73] Assignee: Kyowa Hakko Kogyo Kabushiki Kaisha, Japan

[21] Appl. No.: 87,128

[22] Filed: Aug. 19, 1987

[30] Foreign Application Priority Data

Aug. 26, 1986 [JP] Japan ................................. 61-199519

[51] Int. Cl.$^4$ ................... C07D 487/14; A61K 31/40
[52] U.S. Cl. .................................................. 548/422
[58] Field of Search ................ 548/422; 514/410, 411

[56] References Cited

U.S. PATENT DOCUMENTS 4,642,352  2/1987  Kaneko et al. ...................... 548/422

OTHER PUBLICATIONS

Wong et al., Chem. Abstracts, vol. 106 (1987), Entry 32718p.

Primary Examiner—Nicholas S. Rizzo
Attorney, Agent, or Firm—Wolder, Gross & Yavner

[57] ABSTRACT

Mitomycin compound having potent antitumour activity having the formula:

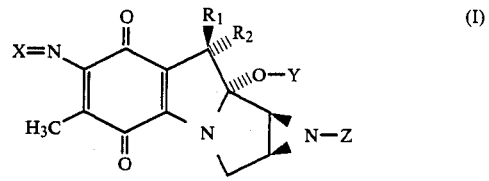

wherein

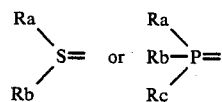

(wherein Ra, Rb and Rc each independently represent lower alkyl, cycloalkyl having 3-7 carbon atoms or phenyl; or Ra and Rb are bonded together to form a poly-methylene group having 2-5 carbon atoms);
one of $R_1$ and $R_2$ represents carbamoyloxymethyl and the other represents hydrogen; or $R_1$ and $R_2$ may together form an exocyclic methylene group;
and Y and Z each independently represents hydrogen or methyl.

6 Claims, No Drawings

MITOMAYCIN COMPOUNDS

The present invention relates to novel mitomycin compounds having antitumour and antibacterial activities.

Mitomycins are known as antibiotics having antitumour and antibacterial activities. Examples of typical mitomycins include mitomycin A, mitomycin B, mitomycin C and porfiromycin, which are referred to in the Merck Index, 10th Edition, mitomycin D and mitomycin E, which are disclosed in JP-A-122797/79, mitomycin F and mitomycin J, which are disclosed in JP-A-45322/80, mitomycin G and mitomycin H, which are disclosed in JP-A-15408/80 and the like. These mitomycins have the chemical structures shown in the following Table 1 and may be obtained by culturing a microorganism of the species *Streptomyces caespitosus*.

TABLE 1
Typical mitomycins from natural sources

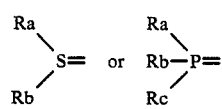

| Mitomycin | $X_A$ | $Y_A$ | $Z_A$ | $R_A$ | $R_B$ |
|---|---|---|---|---|---|
| A | $OCH_3$ | $CH_3$ | H | a | H |
| B | $OCH_3$ | H | $CH_3$ | H | a |
| C | $NH_2$ | $CH_3$ | H | a | H |
| D | $NH_2$ | H | $CH_3$ | H | a |
| E | $NH_2$ | $CH_3$ | $CH_3$ | H | a |
| F | $OCH_3$ | $CH_3$ | $CH_3$ | a | H |
| G | $NH_2$ | $CH_3$ | $CH_3$ | * | * |
| H | $OCH_3$ | H | $CH_3$ | * | * |
| J | $OCH_3$ | $CH_3$ | $CH_3$ | H | a |
| Porfiromycin | $NH_2$ | $CH_3$ | $CH_3$ | H | a |

Notes:
*Bonded together to form $=CH_2$
a $-CH_2OCONH_2$

Among these mitomycin compounds, mitomycin C is widely used for clinical purposes in view of its especially high antitumor activity. However, in view of its high toxicity, in particular to bone marrow, various derivatives of mitomycin compounds have been proposed to increase antitumour activity and/or decrease high toxicity.

Certain known derivatives of mitomycin contain a substituted amino group at the 7th position. However, only JP-A-169481/85 discloses derivatives in which the 7-amino group is substituted by a group linked through an atom other than carbon. More particularly, this specification discloses mitomycin derivatives in which the 7-amino group is substituted, for example, by a methanesulfonylamino group (in Example 5) or a diethylthiophosphorylamino group viz. $(C_2H_5)_2P(=S)NH-$ (in Example 14).

Also known are mitomycin derivatives in which two hydrogen atoms at the 7-amino group are substituted to form $=N-$ (the 7th position) such as, for example, 7-N-(dimethylaminomethylene)mitomycin C, which is disclosed in JP-A-1486/84 and is referred to as 7-N-(dimethylaminomethylene)amino-9a-methoxymitosane; and 7-N-(dimethylaminomethylene)mitomycin D, which is disclosed in JP-A-176590/86.

There has long been a need to provide new and useful mitomycin derivatives. The present invention now provides novel mitomycin derivatives in which the 7th position is substituted by $S=N-$ or $P=N-$ and which exhibit excellent antitumour activity.

According to the present invention there are provided mitomycin derivatives having excellent antitumour activity and having the formula:

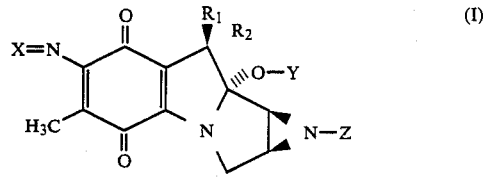

wherein X is

(wherein Ra, Rb and Rc each independently represent lower alkyl, cycloalkyl having 3–7 carbon atoms or phenyl; or Ra and Rb are bonded together to form a polymethylene group having 2–5 carbon atoms);
one of $R_1$ and $R_2$ represents carbamoyloxymethyl and the other represents hydrogen; or $R_1$ and $R_2$ may together form an exocyclic methylene group;
and Y and Z each independently represents hydrogen or methyl.

In the following specification, compounds represented by this formula are referred to as Compounds (I). Compounds represented by other formulae are referred to similarly.

With regard to the definition of Ra, Rb and Rc in formula (I), lower alkyl groups may be straight or branched alkyl groups having 1–4 carbon atoms such as, for example, methyl, ethyl, i-propyl, or n-butyl; cycloalkyl having 3–7 carbon atoms are exemplified by cyclopropyl, cyclopentyl or cyclohexyl; and polymethylene group having 2–5 carbon atoms are exemplified by tetramethylene, pentamethylene and the like.

Compounds (I) in which X represents

may be prepared by the reaction of a mitomycin derivative having an alkoxy, acyloxy or a di-lower alkylaminomethyleneamino group at the 7th position with a sulfilimine represented by the formula:

$$\begin{array}{c}Ra\\ \diagdown\\ \quad S=NH\\ \diagup\\ Rb\end{array} \quad (II)$$

[wherein Ra and Rb are as hereinbefore defined in formula (I)] or an acid addition salt thereof in an inert solvent. In the case where an acid addition salt thereof is used, the reaction is carried out under basic conditions.

The reactions of mitomycins having an acyloxy or a di-lower alkyl-aminomethyleneamino group with amines are disclosed in JP-A-73085/81 and 1486/84, respectively.

It is preferred to use mitomycins having an alkoxy group, in particular, 7-methoxymitomycins. Although Compounds (I) may be prepared with reference to, for example, Journal of Antibiotics, 189 (1968), which discloses the reaction of 7-methoxymitomycins with alkylamines, their preparation is described in the following:

Examples of 7-methoxymitomycins include mitomycin A, mitomycin B, mitomycin F, mitomycin H and mitomycin J.

Inert solvents which may be used for the reaction are exemplified by ether-type solvents such as diethylether and teterahydrofuran; aromatic hydrocarbons such as benzene and toluene; halogenated alkanes such as methylene chloride and chloroform; acetonitrile, dimethylformamide, dimethylsulfoxide and the like, any of which may be used alone or in admixture. Suitable bases for providing basic conditions are exemplified by sodium carbonate, sodium bicarbonate, pyridine, triethylamine and the like.

Usually an equimolar amount of Compound (II) to 7-methoxymitomycin is used but optionally higher ratios, for example, 1–3 moles of Compound (II) per mole of 7-methoxymitomycin may be used to obtain Compound (I) with higher yield.

The reaction conditions may vary, depending upon the type and amount of the used Compound (II). However, it is preferred to carry out the reaction at a temperature of from $-25°$ to $25°$ C., and the reaction is usually continued for a period of from 1 to 18 hours.

The synthesis of Compounds (II) is disclosed, for example, in Tetrahedron Lett., 1619 (1972) and J. Org. Chem., 41, 1728 (1976). Compounds (II) may be obtained by decomposition of a starting material viz. a compound of the formula:

[wherein Ra and Rb are as hereinbefore defined in formula (I)] by the use of concentrated sulfuric acid, followed by neutralization with a base. The resultant Compounds (II) may be used, without further purification and isolation, for the reaction with 7-methoxymitomycin.

Compounds (I) in which X represents

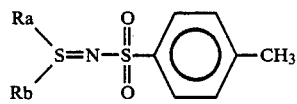

may be prepared by reacting a mitomycin derivative having an alkoxy, acyloxy or di-lower alkyl-aminomethyleneamino group at the 7th position with a compound of formula (III):

  (III)

[wherein Ra, Rb and Rc are as hereinbefore defined in formula (I)] or an acid addition salt thereof, in an inert solvent. In the case of using an acid addition salt of Compound (III), the reaction is carried out under basic conditions. The synthesis of Compounds (III) is disclosed in Method Chim., 7, 529 (1978).

However, Compounds (I) in which X represents

may also be simply prepared by the reaction of a mitomycin derivative having an amino group at the 7th position with a phosphine represented by the following formula (IV):

  (IV)

[wherein Ra, Rb and Rc are as herebefore defined in formula (I)] in the presence of dialkyl azodicarboxylate in an inert solvent.

Although the reaction of this type is exemplified in Tetrahedron Lett., 4031 (1978), the application of such a reaction to a compound having a complicated structure such as, for example, mitomycin has not yet been reported in the art.

Preferred 7-aminomitomycins which may be used for this reaction are exemplified by mitomycin C, mitomycin D, mitomycin E, mitomycin G and porfiromycin. Examples of Compounds (IV) include triethylphosphine, tributylphosphine, triphenylphosphine and the like. Solvents which may be used for this reaction are exemplified by ether-type solvents such as diethyl ether and tetrahydrofuran and anhydrous solvents such as, benzene, methylene chloride and hexamethylphosphorous triamide, any of which may be used alone or in admixture.

Usually, diethyl ester and diisopropyl ester may be used as dialkyl azodicarboxylate. Each of Compounds (IV) and dialkyl azodicarboxylate may be used in an equimolar amount to 7-aminomitomycin. However, higher ratios for example, 1–3 moles per mole of 7-aminomitomycin may, if desired, be used to obtain the desired product with higher yield.

The reaction conditions may vary, depending upon the amounts of Compound (IV) and dialkyl azodicarboxylate used. Usually, the reaction is carried out at a temperature of from $-25°$ to $25°$ C. and is continued for a period of 1 to 6 hours.

After completion of each of the reactions as set forth, the reaction solution is purified with or without concentration using conventional techniques. Alternatively, the reaction solution is extracted with a suitable anhydrous solvent such as, for example, chloroform, methylene chloride and ethyl acetate. The extracted solution is washed with water which may, if desired, contain sodium bicarbonate, followed by concentration. The concentrate is then purified. Purification may be effected, for example, by column chromatography, TLC, recrystallization and the like.

As shown hereinafter, Compounds (I) may be used as an antibacterial and antitumour agents in view of their excellent antitumour and antibacterial activities. In particular, in formula (I) wherein (A) represents

and both Ra and Rb each independently represent lower alkyl, or (B) X is

and one of Ra and Rb represents lower alkyl and the other represents phenyl,

Compounds (I) exhibit higher chemotherapeutic index (C.I.) values than the C.I. value of mitomycin C and lower bone marrow toxicities than the corresponding toxicity of mitomycin C.

C.I. value ($LD_{50}/ED_{50}$) reflects the selective toxicity against tumour so that a greater C.I. value suggests a superior antitumour agent and accordingly a wider tolerance of dosage when administered as an antitumour agent. Thus, C.I. value is one of the most important criteria for antitumour agents.

Among Compounds (I) having a phosphorus-containing group, certain compounds in which X represents

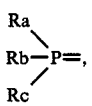

and Ra=Rb=Rc, are advantageous in view of their pharmacological effects and production efficiency.

Compounds (I) may be used for the preparation of antitumour and/or antibacterial pharmaceutical compositions comprising as active ingredient an effective amount of a Compound (I) in association with at least one pharmaceutically acceptable carrier and/or adjuvant. Thus such compositions may contain, for example, diluents, additives, carriers and the like conventionally used in pharmacy.

The Compounds (I) also have utility as intermediates for the preparation of other compounds having antitumour activity.

Each of Compounds (I) may be administered to animals in various forms and in particular, to humans, for example, at a dosage of 0.06–5 mg/kg by intravenous injection. In this case, Compounds (I) may be dissolved, for example, in physiological saline, solutions of glucose, lactose or mannitol and the like. The injection may preferably be intravenous, although it is possible to administer, for example, by the intraarterial, abdominal or pleural routes. The compositions for administration may be freeze-dried according to the Pharmacopoeia of Japan. It is also possible to add sodium chloride to Compounds (I) to obtain injection powders. Further, various salts and the like, which are well known in the pharmaceutical art, may be added to Compounds (I) as diluents such as for example, Ringer's solution; additives such as for example, polyethyleneglycol, HCO-60 (surfactant; commercial product of Nikko Chemicals K.K., Japan), ethanol and/or suitable carriers such as for example, lypozome, cyclodextrin.

The optimum dose of Compounds (I) may vary, depending upon the particular Compound (I), the age of the patients, the symptoms and the like.

Administration schedule may vary, depending upon the dosage, the symptoms and the like, and the composition containing the Compound (I) may be administered, for example, once per week, or once per three weeks.

It is possible to administer the same amount of Compounds (I) by oral or rectal route and suitable compositions may be prepared in conventional manner. For oral administration, it is preferred to formulate Compounds (I) and suitable additives into tablets, powders or granules. Suppositories may also be used for administration.

Certain Compounds (I) exhibit hydrophilic or hydrophobic properties, which can give rise to good results in some cases. For example, hydrophilicity is advantageous for an injection agent. Compounds (I) in which X is

and both Ra and Rb are lower alkyl groups, are highly water-soluble.

Our invention is illustrated in the following Examples and Formulations.

EXAMPLES

In the following examples, the physico-chemical data was determined by means of the following devices:

NMR: FX-100 (100 MHz), commercial product of Nihon Denshi K.K., Japan or AM-400 (400 MHz), commercial product of Bruker, West Germany.

MS: M-800 (by EI or SI method), commercial product of Hitachi Limited, Japan.

TLC: Silica gel plate Art. 5714, commercial product of Merck AG., West Germany.

Table 2 shows the structures of typical Compounds (I) synthesized.

TABLE 2

Typical Compounds (I)

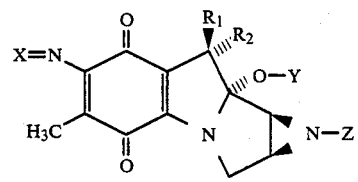

| No. | X | $R_1$ | $R_2$ | Y | Z |
|---|---|---|---|---|---|
| 1 | $(C_6H_5)_2S$ | $CH_2OCONH_2$ | H | $CH_3$ | H |
| 2 | $(C_6H_5)_2S$ | H | $CH_2OCONH_2$ | H | $CH_3$ |
| 3 | $(C_6H_5)_2S$ | =$CH_2$ | | H | $CH_3$ |
| 4 | (Z)—$C_6H_5$, $CH_3S$ | $CH_2OCONH_2$ | H | $CH_3$ | H |
| 5 | (E)—$C_6H_5$, $CH_3S$ | =$CH_2$ | | $CH_3$ | H |
| 6 | $(C_2H_5)_2S$ | =$CH_2$ | | $CH_3$ | H |
| 7 | $(C_2H_5)_2S$ | H | $CH_2OCONH_2$ | H | $CH_3$ |
| 8 | $(CH_3)_2S$ | =$CH_2$ | | H | $CH_3$ |
| 9 | $(C_6H_5)_3P$ | $CH_2OCONH_2$ | H | $CH_3$ | H |
| 10 | $(n-C_4H_9)_3P$ | =$CH_2$ | | $CH_3$ | H |

EXAMPLE 1

7-demethoxy-7-diphenylsulfiliminomitomycin A (Compound 1)

Mitomycin A (211 mg) was dissolved in a mixture of benzene/chloroform (8 ml; 1:1 v/v). Diphenylsulfilimine (138 mg) was added to the solution while stirring. 16 hours after this, the reaction solution was directly subjected to silica gel column chromatography using a solvent system of chloroform/methanol (94:6 v/v) for elution.

Fractions showing dark greenish band were collected and combined. The solvent was removed from the combined fractions by evaporation under reduced pressure to obtain dark greenish solid. By recrystallization using acetone, dark greenish prism crystals (298 mg) were obtained as Compound 1 with a yield of 95%.

Similarly, Compound 2 and 3 were obtained.

EXAMPLE 2

(Z)-7-demethoxy-7-methylphenylsulfiliminomitomycin A (Compound 4) and (E)-7-demethoxy-7-methylphenylsulfilimino mitomycin A (Compound 5)

Methylphenyl-N-p-tolsylsulfilimine (150 mg) was dissolved in concentrated sulfuric acid (150 μl) and heated at 40° C. under nitrogen stream. 20 minutes after this, cold ether (1 ml) was added to the solution, followed by stirring for 30 minutes while cooling with ice. After removing the ether layer from the reaction solution by decantation, the solution was cooled at −78° C. Anhydrous aqueous ammonia (2 ml) was added to the solution, followed by stirring for 1.5 hours. Ammonia was removed from the solution at −15° C. Mitomycin A (73 mg) dissolved in acetonitrile (3 ml) was added to the solution under nitrogen stream, and the mixture was stirred for 2 hours. Small pieces of dry ice were added to the reaction mixture to stop the reaction. The reaction solution was filtered by using cellite, followed by washing with chloroform (10 ml). The filtrate was directly subjected to silica gel chromatography using a solvent system of chloroform/methanol (9:1 v/v) for elution. Fractions showing a Rf at 0.34 and fractions showin a Rf at 0.27 by means of TLC using a same solvent system were respectively collected and combined.

On each occasion, the solvent was removed by evaporation under reduced pressure. The residue was dissolved in a small amount of acetone, and precipitated by adding n-hexane. The solvent was removed from the solid material by evaporation under reduced pressure, and was further removed completely from the residue at room temperature. Dark greenish prism crystals were obtained showing a Rf at 0.34 (Compound 4: 28 mg; yield 41%) and greenish powders showing a Rf at 0.27 (Compound 5: 25 mg; yield 37%). Similarly, Compounds 6–8 were obtained.

Compound 6 exhibited a water-solubility of more than 40 mg/ml.

EXAMPLE 3

7-demethoxy-7-triphenylphosphiniminomitomycin A (Compound 9)

Triphenylphosphine (131 mg; hereinafter referred to as TPP) and diisopropyl azodicarboxylate (98 μl; hereinafter referred to as DIAD) were dissolved in anhydrous tetrahydrofuran (1 ml; hereinafter referred to as THF) and stirred for 30 minutes in nitrogen atmosphere while cooling with ice water. This solution was diluted with addition of anhydrous THF (3 ml) containing mitomycin C (67 mg). The mixture was stirred for 5.5 hours at room temperature. The reaction solution was diluted with addition of ethyl acetate (30 ml) and washed with saturated solution of sodium bicarbonate. After removal of the ethyl acetate layer, the sodium bicarbonate layer was extracted with ethyl acetate. After washing with saturated sodium chloride solution and saturated sodium bicarbonate solution, the combined solutions were dried by using anhydrous sodium sulfate. The drying agent was removed from the reaction solution by filtration, and then the solvent was removed from the solution by evaporation under reduced pressure. The residue was subjected to silica gel column chromatography using a solvent system of chloroform/acetone (7:3 v/v). After this, elution was effected by using a solvent system of chloroform/methanol (94:6 v/v). Fractions showing a dark greenish band at a Rf of 0.34 were collected and combined, from which the solvent was then removed by evaporation under reduced pressure. The residue was dissolved in a small amount of chloroform. The material was precipitated with addition of n-hexane, from which the solvent was removed by evaporation under reduced pressure. The residue was then completely dried for 12 hours at 25° C./1 mmHg to obtain Compound 9 (81 mg) in the form of dark Greenish powders with a yield of 68%.

Similarly, Compound 10 was prepared. The starting material, yield and appearance of each of Compounds 1 to 10 are shown in Table 3 and their MS and NMR data are shown in Table 4.

TABLE 3

Synthesis of typical Compounds (I)

| Materials | Product Compound | Yield | Appearance |
| --- | --- | --- | --- |
| Mitomycin A (211 mg)<br>(C6H5)2S=NH (138 mg) | No. 1 | 95 | Dark greenish prism |
| Mitomycin B (216 mg)<br>(C6H5)2S=NH (151 mg) | No. 2 | 96 | Greenish powder |
| Mitomycin H (130 mg)<br>(C6H5)2S=NH (116 mg) | No. 3 | 69 | Dark greenish prism |
| Mitomycin A (73 mg)<br>C6H5, CH3S=N—Ts<br>(150 mg) | No. 4 | 41 | Dark greenish prism |
| Mitomycin A (73 mg)<br>C6H5, CH3S=N—Ts<br>(150 mg) | No. 5 | 37 | Greenish powder |
| Mitomycin A (100 mg)<br>(C2H5)2S=N—Ts (300 mg) | No. 6 | 16 | Greenish powder |
| Mitomycin B (134 mg)<br>(C2H5)2S=N—Ts (300 mg) | No. 7 | 10 | Dark greenish prism |
| Mitomycin B (128 mg)<br>(CH3)2S=N—Ts (300 mg) | No. 8 | 28 | Greenish powder |
| Mitomycin C (67 mg)<br>TPP (131 mg)<br>DIAD (98 μl) | No. 9 | 68 | Dark greenish powder |
| Mitomycin C (67 mg)<br>TBP (125 μl)<br>DIAD (98 μl) | No. 10 | 22 | Dark greenish powder |

Note:
TBP = [CH3(CH2)3]3P

Ts = SO2— 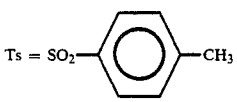 —CH3

TABLE 4

MS and NMR data of typical Compounds (I)

| No. | MS | NMR(δ) |
|---|---|---|
| 1 | (EI)m/z518=M+<br>$C_{27}H_{26}N_4O_5S=518$ | (100 MHz,Py-d$_5$)1.28(1H,bs), 2.48 (3H,s), 2.71(1H,dd,J=4.4,1.7), 3.10(1H,d,J=4.4), 3.10(3H,s), 3.62(1H,dd,J=12.7,1.7), 3.84(1H, dd,J=11.0,4.4), 4.73(1H,d,J=12.7) 4.99(1H,dd,J=11.0,10.4), 5.29(1H, dd,J=10.4,4.4), 7.36(6H,m), 7.58 (2H,bs), 8.00(4H,m) |
| 2 | (EI)m/z518=M+<br>$C_{27}H_{26}N_4O_5S=518$ | (100 MHz,Py-d$_5$) 2.04(3H,s), 2.18 (1H,dd,J=4.6,1.8), 2.40(1H,d,J=4.6), 2.45(3H,), 3.72(1H,dd,J=12.9,1.8), 4.10(1H,dd,J=10.3,3.7) 4.63(1H,d,J=12.9), 5.17(1H,t,J=10.3), 5.43(1H,dd,J=10.3,3.7), 7.36(6H,m), 7.50(2H,bs), 7.96(4H, m), ~8.3 (1H,bs) |
| 3 | (EI)m/z457=M+<br>$C_{26}H_{23}N_3O_3S=457$ | (100 MHz, Py-d$_5$) 2.10(3H,s), 2.25 (1H,dd,J=4.6,1.7), 2.42(3H,s), 2.58(1H,d,J=4.6), 3.78(1H,dd,J=12.7,1.7), 4.95(1H,d,J=12.7), 5.69(1H,d,J=1.5), 6.30(1H,d,J=1.5), 7.36(6H,m), 7.92(4H,m), ~8.9 (1H,bs) |
| 4 | (EI)m/z456=M+<br>$C_{22}H_{24}N_4O_5S=456$ | (400 MHz, CDCl$_3$) 0.60(1H,bs), 2.01 (3H,s), 2.79(1H,bs), 2.84(1 H,bs), 2.88(3H,s), 3.21(3H,s), 3.54(1H,bd,J=13.0),3.57(1H,dd,J=10.6,4.3), 4.39(1H,bt), 4.45(1H,d, J=13.0), 4.58(1H,dd,J=10.6,4.3), 4.67(2H,bs), 7.53(3H,m), 7.77(2 H,m) |
| 5 | (EI)m/z456=M+<br>$C_{22}H_{24}N_4O_5S=456$ | (400 MHz, CDCl$_3$) 0.60(1H,bs), 2.01 (3H,s), 2.79(1H,bs), 2.87(1 H,bs), 2.88(3H,s), 3.18(3H,s), 3.54(1H,bd,J=13.0), 3.55(1H,dd,J=10.7,4.2), 4.46(1H,d,J=13.0), 4.46(1H,bt), 4.72(2H,bs), 4.75(1 H,dd,J=10.7,4.2), 7.53(3H,m), 7.79(2H,m) |
| 6 | (EI)m/z422=M+<br>$C_{19}H_{26}N_4O_5S=422$ | (400 MHz, CDCl$_3$) ~0.6(1H), 1.33(3H,t,J=7.4), 1.34(3H,t,J=7.4), 1.91(3H,s), 2.79(1H,bd,J=4.2), 2.87(1H,d,J=4.2), 3.00(4H, m), 3.21(3H,s),3.55(1H,dd,J=13.0, 1.5),3.60(1H,dd,J=10.8,4.2),4.44 (1H,dd,J=10.8,10.7), 4.49(1H,d,J=13.0), 4.72(2H,bs), 4.77(1H,dd, J=10.7,4.2), |
| 7 | (EI)m/z422=M+<br>$C_{19}H_{26}N_4O_5S=422$ | (100 MHz, CDCl$_3$)1.32(3H,t,J=7.4) 1.34(3H,t,J=7.4), 1.86(3H,s), 2.26(5H,s), 2.95(4H,m),3.55(1H, bd,J=13.2), 3.69(1H,t,J=4.9), 4.31(1H,d,J=13.2), 4.38(1H,bs), 4.71(2H,d,J=4.9), 4.79(2H,bs) |
| 8 | (SI)m/z395=M+ +1<br>$C_{17}H_{22}N_4O_5S=394$ | (100 MHz,Py-d$_5$) 2.12(3H,s), 2.21 (1H,dd,J=4.4,1.7), 2.30(3H,s), 2.48(1H,dd,J=4.4), 2.50(3H,s), 2.57(3H,s), 3.74(1H,dd,J=12.9, 1.7), 4.27(1H,dd,J=10.0,3.7), 4.73(1H,d,J=12.9), 5.24(1H,dd,J=10.3,10.0), 5.54(1H,dd,J=10.3, 3.7), 7.56(2H,bs), 8.38(1H,bs) |
| 9 | (EI)m/z594=M+<br>$C_{33}H_{31}N_4O_5P=594$ | (400 MHz,Py-d$_5$) 1.94(1H,bs), 2.59 (3H,s), 2.67(1H,bs), ~3.0 (1H,bs), 3.03(3H,s), 3.57(1H,bd, J=12.7), 3.67(1H,dd,J=11.0,4.1), 4.55(1H,d,J=12.7), 4.82(1H,dd,J=10.3,4.1), 4.92(1H,dd,J=11.0, 10.3),7.40(9H,bs),18 7.5(2H,bs), 8.00(6H,m) |
| 10 | (EI)m/z535=M+ +1<br>$C_{27}H_{43}N_4O_5P=534$ | (400 MHz,Py-d$_5$) 0.84(9H,t,J=7.3), 1.33 (6H,sex,J=7.3), 1.52(6H,sex, J=7.3), 2.02(1H,bs), 2.08(6H,m), 2.38(3H,s), 2.74(1H,bs), 3.17(1 H,bs), 3.19(3H,s),3.62(1H,bd,J=12.7), 4.00(1H,dd,J=11.1, 4.1), 4.67(1H,d,J=12.7), ~5.2(1H),5.37 (1H,dd,J=10.3,4.1), ~7.6(2H,bs) |

FORMULATION 1

Compound 6 (3 g) is dissolved in distilled water (1000 ml) and sterilized under pressure by means of Millipore filter (pore diameter 0.22μ). The sterilized filtrate is divided into fractions which were put into vials (1.0 ml in each vial), which contains 3 mg of the active ingredient. Each vial is freeze-dried at −50° C. for 2 hours. The primary drying is effected under pressure (0.1 mmHg) at a shelf temperature of −10° C. for 24 hours. After the shelf temperature reaches the temperature of the article, the secondary drying is carried out under reduced pressures (0.1 mmHg) at the shelf temperature of 30° C. for 4 hours to remove moisture. Then each vial is sealed. Prior to use, sterilized physiological saline (5 ml) is put into the vial which is shaken to dissolve the ingredient. In this manner, there is obtained an injection agent.

The following Experiments illustrate the pharmacological effects of typical Compounds (I).

EXPERIMENT 1

Antibacterial activities of Compounds (I) against various microorganisms are shown in the following Table 5, in which the minimum inhibitory concentration MIC (μg/ml) was measured by the agar dilution method at a pH of 7.0.

TABLE 5

Antibacterial activities of typical Compounds (I) (Minimum inhibitory concentration, μg/ml)

| Compound | SF | SA | BS | PV | KP |
|---|---|---|---|---|---|
| 1 | 0.02 | 0.01 | <0.005 | 0.63 | 0.16 |
| 2 | 0.78 | 0.78 | 0.2 | — | 25 |
| 3 | — | — | 0.63 | — | — |
| 6 | 0.078 | 0.039 | 0.020 | 0.039 | 0.039 |
| 7 | 20 | 10 | 5.0 | 20 | 10 |
| 9 | 13 | 13 | 3.1 | 25 | 13 |

In this table, the following abbreviations are used: SF-*Streptococcus faecalis* ATCC 10541; SA-*Staphylococcus aureus* ATCC6538P; BS-*Bacillus subtilis* 10707; PV-*Proteus vulgaris* ATCC6897; KP-*Klebsiella pneumoniae* ATCC10031.

EXPERIMENT 2

Antitumour activity against Sarcoma 180 solid tumour and toxicity:

Certain Compounds (I) and Sarcoma 180 solid tumour were used to determine, on each occasion, antitumour activity (ED$_{50}$), acutee toxicity (LD$_{50}$) and effect upon peripherical leucocytes (WBC$_{4000}$), as shown Table 6.

TABLE 6

Antitumour activities and toxicities of typical Compounds (I)

| Com. No. | LD$_{50}$ mg/kg | ED$_{50}$ mg/kg | C.I. | WBC$_{4000}$ mg/kg |
|---|---|---|---|---|
| 2 | >200 | 89.1 | >2.2 | >200 |
| 3 | >200 | 132.1 | >1.5 | >200 |
| 5 | 15.0 | 2.7 | 5.6 | 4.1 |
| 6 | 9.4 | 2.5 | 3.8 | 5.6 |
| 9 | >100 | 100 | ≧1.0 | >100 |

Notes:
(1) C.I.: LD$_{50}$/ED$_{50}$
(2) WBC$_{4000}$ denotes the minimum dose capable of decreasing the number of peripheral leucocytes to 4000/mm$^3$.

The experiments were carried out in the following manner.

(1) Effect upon Sarcoma 180 solid tumour:

$5 \times 10^6$ cells of Sarcoma 180 solid tumour were abdominally implanted into a ddy mouce. 7 days after this, the cells were collected from the ascites fluid. The cells were washed once with physiological saline under sterile conditions and suspended in physiological saline to obtain a cell suspension containing $5 \times 10^7$ cells/ml, of which 0.1 ml was implanted into a ddy male mouce (body weight 20±2 g) under the skin of the right armpit. The test compound was dissolved in physiological saline or the same solution containing Tween 80. 24 hours after implantation of the tumour cells, 0.1-0.2 ml of the solution containing the test compound was administered to the tail vein of each animal in the test group consisting of 5 animals. 7 days after the implantation, the major axis (a) and minor axis (b) of the tumour were measured to calculate the volume of the tumour as ("a"×"b$^2$")/2. The antitumour effect was indicated by T/C which is the ratio of the tumour volume in the test animals to the corresponding volume of the control (untreated) animals.

(2) ED$_{50}$:

ED$_{50}$ denotes the dosage capable of decreasing the volume of Sarcoma 180 solid tumour to 50% of the corresponding volume of the control animals. T/C ratios and the dose were respectively plotted on the ordinate using an arithmetic scale and on the abscissa using a logarithmic scale, the relationship between the dosage and the T/C ratio being converted to a straight line by the least squares method. From the straight tropic line thus-obtained, the dosage corresponding to a T/C=0.5 viz. ED$_{50}$ was determined.

(3) Acute toxicity

The test compound was abdominally administered once to ddy mice, each group consisting of 5 animals. After this, the death ratio of the animals of the test group was observed for 14 days, from which LD$_{50}$ was calculated by Behrens-Körber's method.

(4) Effect upon peripheral leucocytes:

Sarcoma 180 solid tumour cells ($5 \times 10^6$) were subcutaneously implanted under the skin of the right armpit of each mouse (body weight 20±2 g) of a group consisting of 5 male mice (ddy strain). 24 hours after this, a test compound was intraperitoneally administered to each animal. 4 days later, blood (0.02 ml) was collected from the suborbital plexus vein of each tumour-carrying animal. The collected sample of blood was dispersed in 9.98 ml of Cellkit Seven solution. One drop of saponin solution was added to the sample to dissolve erythrocytes and then a microcell counter was used to measure the number of leucocytes. On graph paper, the number of leucocytes was plotted on the ordinate using an arithmetic scale, and the dosage was plotted on the abscissa using a logarithmic scale to show the relationship of the dosage to the number of peripherical leucocytes, from which the value of WBC$_{4000}$ viz. a value capable of giving 4000 peripheral leucocytes per mm$^3$ (about half of the corresponding value in normal mice) was obtained.

We claim:

1. Mitomycin compounds represented by the formula:

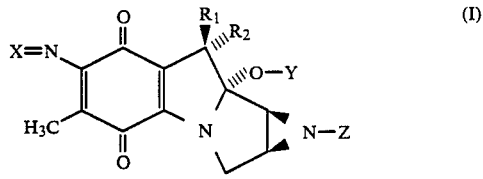

wherein
X is

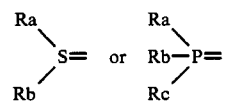

(wherein Ra, Rb and Rc each independently represent lower alkyl, cycloalkyl having 3–7 carbon atoms or phenyl; or Ra and Rb are bonded together to form a poly-methylene group having 2–5 carbon atoms);

one of R$_1$ and R$_2$ represents carbamoyloxymethyl and the other represents hydrogen; or R$_1$ and R$_2$ may together form an exocyclic methylene group;

and Y and Z each independently represents hydrogen or methyl.

2. Mitomycin compounds according to claim 1 wherein X represents

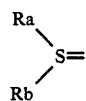

and both Ra and Rb each independently represent lower alkyl.

3. Mitomycin compounds according to claim 1 wherein X represents

and one of Ra and Rb represents lower alkyl and the other represents phenyl.

4. Mitomycin compounds according to claim 1 wherein X represents

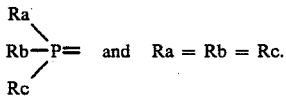

5. (E)-7-demethoxy-7-methylphenylsulfilimino mitomycin A.

6. 7-demethoxy-7-diethylsulfiliminomitomycin A.

* * * * *